(12) United States Patent
Major et al.

(10) Patent No.: US 11,517,361 B2
(45) Date of Patent: Dec. 6, 2022

(54) FIXATION DEVICE AND METHOD OF USING THE SAME

(71) Applicant: K2M, Inc., Leesburg, VA (US)

(72) Inventors: Eric Major, Purcellville, VA (US); Thomas J. Errico, New York, NY (US); Peter Newton, La Jolla, CA (US); Harry Shufflebarger, Jupiter, FL (US); Larry E. McClintock, Gore, VA (US)

(73) Assignee: K2M, Inc., Leesburg, VA (US)

( * ) Notice: Subject to any disclaimer, the term of this patent is extended or adjusted under 35 U.S.C. 154(b) by 403 days.

(21) Appl. No.: 16/499,013

(22) PCT Filed: Mar. 30, 2018

(86) PCT No.: PCT/US2018/025378
§ 371 (c)(1),
(2) Date: Sep. 27, 2019

(87) PCT Pub. No.: WO2018/183830
PCT Pub. Date: Oct. 4, 2018

(65) Prior Publication Data
US 2021/0113250 A1    Apr. 22, 2021

Related U.S. Application Data

(60) Provisional application No. 62/478,696, filed on Mar. 30, 2017.

(51) Int. Cl.
*A61B 17/86* (2006.01)
*A61B 17/70* (2006.01)
*A61B 17/84* (2006.01)

(52) U.S. Cl.
CPC ........ *A61B 17/864* (2013.01); *A61B 17/7082* (2013.01); *A61B 17/844* (2013.01);
(Continued)

(58) Field of Classification Search
CPC .......... A61B 17/7266; A61B 17/7258; A61B 17/844; A61B 2017/8655; A61B 17/8685;
(Continued)

(56) References Cited

U.S. PATENT DOCUMENTS 5,827,285 A * 10/1998 Bramlet ................. A61B 17/80
606/328
7,635,379 B2 * 12/2009 Callahan ............ A61B 17/8685
606/247
(Continued)

FOREIGN PATENT DOCUMENTS

WO    2018136602 A1    7/2018

OTHER PUBLICATIONS

Medical Design Briefs. Fixating on Innovation. A revolution in Spinal Fusion Surgery. Mar. 1, 2017, p. 1 of 2, First Paragraph to second paragraph; p. 1 of 2, Right Firstand Second Images; p. 2 of 2, Fourth paragraph, Right Image. (Year: 2017).*

(Continued)

*Primary Examiner* — Julianna N Harvey
(74) *Attorney, Agent, or Firm* — Lerner, David, Littenberg, Krumholz & Mentlik, LLP

(57) ABSTRACT

A fixation device includes a tapered cannula defining a bore therethrough, a shaft, and a post. The shaft includes a proximal portion disposed within the bore, and central and distal portions extending distally from the tapered cannula. The proximal portion includes a threaded inner surface defined therein. The shaft includes blades disposed within the central portion, the blades movable between a closed position in which the blades are disposed within the shaft and an open position in which the blades extend laterally through the shaft. The post includes a threaded outer surface threadingly engaged with the threaded inner surface of the (Continued)

shaft. The post is movable longitudinally within the shaft to transition the blades between the closed and open positions.

20 Claims, 13 Drawing Sheets

(52) U.S. Cl.
CPC ...... *A61B 17/8625* (2013.01); *A61B 17/8685* (2013.01); *A61B 2017/8655* (2013.01)

(58) Field of Classification Search
CPC . A61B 17/864; A61B 17/686; A61B 17/7064; A61B 17/8047; A61B 17/7082; A61B 17/8625
USPC .................................. 606/246–289, 300–328
See application file for complete search history.

(56) References Cited

U.S. PATENT DOCUMENTS

| | | | |
|---|---|---|---|
| 8,814,919 B2 | 8/2014 | Barrus et al. | |
| 9,393,049 B2 | 7/2016 | Jones et al. | |
| 2004/0133207 A1* | 7/2004 | Abdou | A61B 17/7059 606/279 |
| 2011/0106172 A1* | 5/2011 | Wallenstein | A61B 17/8685 606/305 |
| 2011/0190830 A1* | 8/2011 | Biedermann | A61B 17/8685 606/305 |
| 2011/0313472 A1* | 12/2011 | Yap | A61B 17/7064 606/305 |
| 2013/0123857 A1* | 5/2013 | Biedermann | A61B 17/84 606/303 |
| 2013/0338722 A1* | 12/2013 | Yalizis | A61B 17/8685 606/312 |
| 2015/0250506 A1* | 9/2015 | Philippon | A61B 17/8891 606/64 |
| 2017/0258498 A1* | 9/2017 | Redmond | A61B 17/7055 |
| 2019/0231405 A1* | 8/2019 | Redmond | A61B 17/8625 |
| 2020/0085478 A1* | 3/2020 | McClintock | A61B 17/7059 |

OTHER PUBLICATIONS

International Search Report including Written Opinion for PCT/US2018/25378 dated Jan. 18, 2019.
Medical Design Briefs, "Fixating on Innovation: A Revolution in Spinal Fusion Surgery," Mar. 1, 2017 downloaded from https://www.medicaldesignbriefs.com./component/content/article/mdb/features/26480 (May 14, 2018 5.05.33 PM).

* cited by examiner

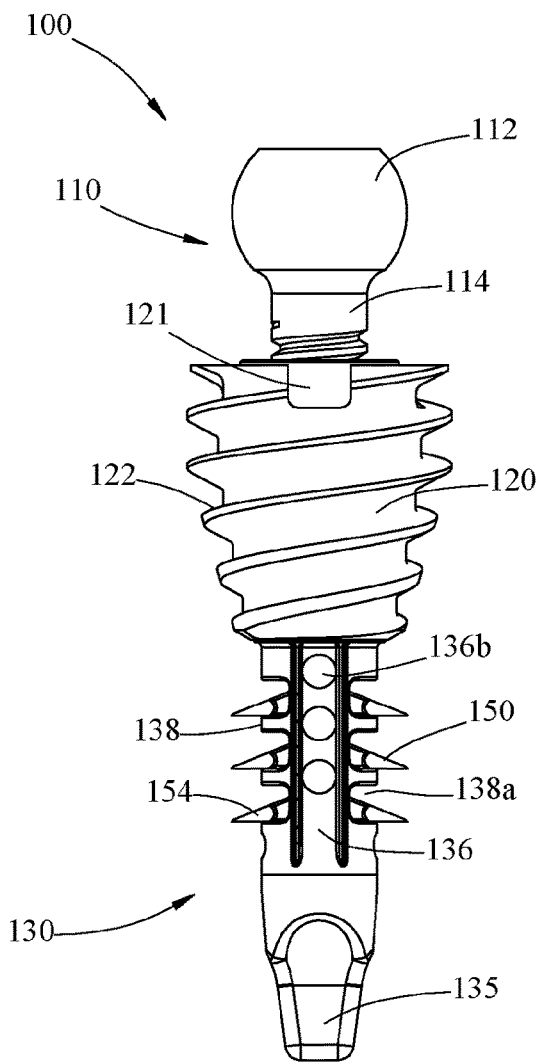
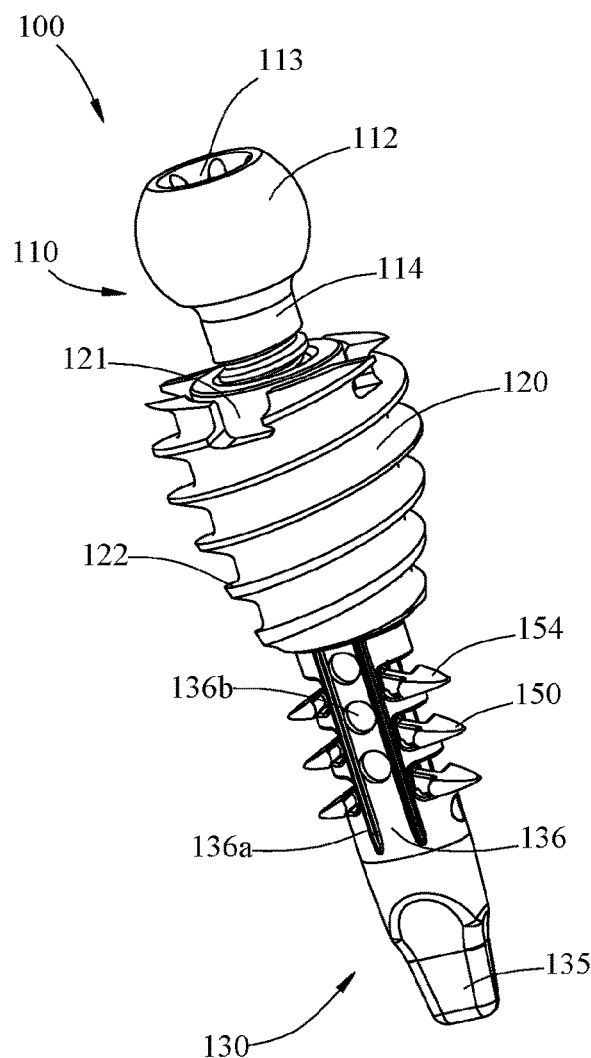
FIG. 2A
FIG. 2B
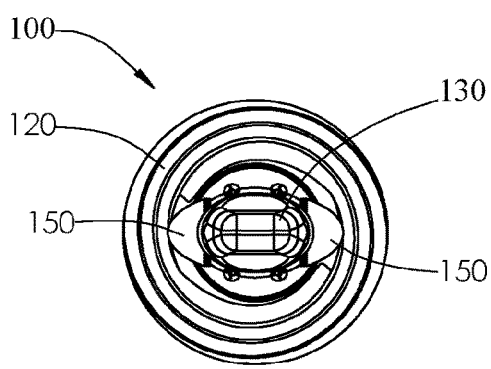
FIG. 2C

FIXATION DEVICE AND METHOD OF USING THE SAME

CROSS-REFERENCE TO RELATED APPLICATION

This application is a national phase entry under 35 U.S.C. § 371 of International Application No. PCT/US2018/025378, filed Mar. 30, 2018, which claims the benefit of the filing date of U.S. Provisional Patent Application No. 62/478,696 filed Mar. 30, 2017, the disclosures of which are hereby incorporated herein by reference.

TECHNICAL FIELD

The present disclosure relates generally to surgical devices, and more particularly, to fixation devices and methods for securing the fixation devices to osseous tissue.

BACKGROUND

During orthopedic surgical procedures, such as replacement of a vertebra of a spinal column, distraction of the spinal column, stabilization of vertebrae, and the like, pedicle screws can be used. A pedicle screw can be screwed into the pedicle of a vertebra and the head of the pedicle screw can be connected to suitable provisions, for example, a stabilizing system, distraction rods, etc.

However, insertion of a pedicle screw, especially multiple pedicle screws, into the spinal column can require a lot of time and effort. Moreover, the act of screwing a pedicle screw into a pedicle in which there is osteoporosis, or bone tissue thinning and loss of bone density, can damage the vertebra.

Fixation devices that can be secured to a vertebra without damaging the vertebra and save time and effort in comparison to a traditional pedicle screw are desirable.

SUMMARY

In accordance with an aspect of the present disclosure, a fixation device includes a tapered cannula defining a bore therethrough, a shaft, and a post. The shaft includes a proximal portion disposed within the bore of the tapered cannula, and central and distal portions extending distally from the tapered cannula. The proximal portion includes a threaded inner surface defined therein. The shaft includes blades disposed within the central portion, the blades movable between a closed position in which the blades are disposed within the shaft and an open position in which the blades extend laterally through the shaft. The post includes a threaded outer surface threadingly engaged with the threaded inner surface of the shaft. The post is movable longitudinally within the shaft to transition the blades between the closed and open positions.

A snap ring may be disposed within an annular groove defined in the bore of the tapered cannula and an annular groove defined in an outer surface of the shaft.

The central portion of the shaft may define blade openings therein and, when the blades are disposed in the open position, each of the blades extends through one of the blade openings. The central portion of the shaft may include spines disposed in opposed relation relative to each other and extending longitudinally between the proximal and distal portions of the shaft. The central portion of the shaft may include ledges that laterally interconnect the spines. In some aspects, when the blades are disposed in the closed position, a portion of each of the blades rests against the respective ledge disposed distal of the blade.

Each blade may include a body portion defining an opening therethrough and a wing portion extending from the body portion. Each blade may include a notch extending from the body portion. The notch may be configured to inhibit rotation of the blade when the blade reaches the open position.

The fixation device may include pins extending through the openings defined in the body portions of the blades, and the blades may be rotatable around the pins.

The fixation device may include aligners, with each aligner including a head disposed within the proximal portion of the shaft, an elongate tail extending into the central portion of the shaft, and a groove extending longitudinally therein. The end portions of each of the pins may be disposed within the grooves of the aligners. The heads of the aligners may be disposed adjacent to and distal of the post such that longitudinal movement of the post causes longitudinal movement of the aligners, the pins, and the blades. Each blade may rotate about the respective pin when the wing portion of the blade contacts a portion of the shaft defining the blade opening in which the respective blade is disposed.

The fixation device may include a cap disposed within the distal portion of the shaft. The cap may include bosses extending from opposed sides of a body, and the bosses may be disposed within the grooves of the aligners. A spring may be disposed within a slot of the cap. The spring may be compressed by the cap when the blades are in the open position and the spring may apply a proximal force on the cap when the blades are in the closed position.

In accordance with another aspect of the present disclosure, a method of securing a fixation device to osseous tissue includes: inserting a shaft and a tapered cannula of a fixation device into an insertion hole in osseous tissue, the fixation device disposed in a closed position in which blades are disposed within the shaft; and applying a force to a post of the fixation device to move the post distally, the post engaged with and longitudinally movable relative to the shaft such that distal movement of the post relative to the shaft causes the fixation device to transition from the closed position to an open position in which the blades extend laterally through the shaft and engage the osseous tissue.

Applying the force to the post may include rotating the post relative to the shaft, the post and the shaft threadingly engaged with each other. Applying the force to the post may include inserting an engagement tip of a driving instrument into an opening defined in a head of the post.

The method may further include applying a force to the post to move the post proximally relative to the shaft to cause the fixation device to transition from the open position back to the closed position.

The method may include applying a rotational force to the tapered cannula to engage helical threads disposed on an outer surface of the tapered cannula with the osseous tissue. Applying the rotational force to the tapered cannula may include inserting tabs of an insertion instrument into cut-outs defined in a proximal end of the tapered cannula.

Other aspects, features, and advantages will be apparent from the description, drawings, and the claims.

BRIEF DESCRIPTION OF THE DRAWINGS

The accompanying drawings, which are incorporated in and constitute a part of this specification, illustrate embodiments of the present disclosure and, together with a general description of the disclosure given above, and the detailed description of the embodiments given below, serve to explain the principles of the present disclosure, wherein:

FIG. 2A is a side view of the fixation device of FIG. 1A, shown in an open position;

FIG. 2B is a perspective view of the fixation device of FIG. 2A;

FIG. 2C is a bottom view of the fixation device of FIG. 2A;

DETAILED DESCRIPTION

Figure 1A:
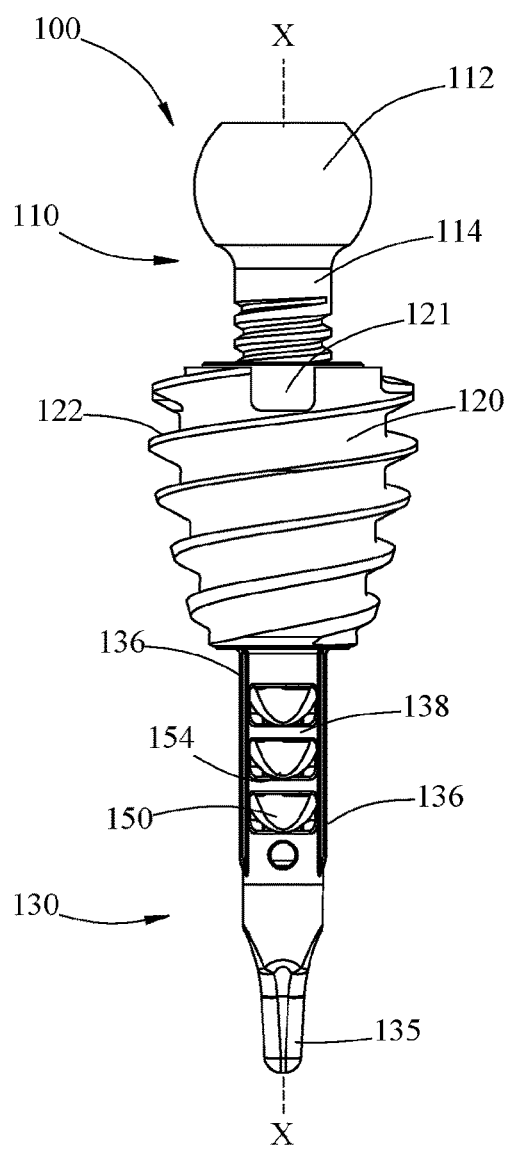
FIG. 1A is a side view of a fixation device in accordance with an embodiment of the present disclosure, shown in a closed position.

Exemplary embodiments of the present disclosure are discussed herein below in terms of a fixation device for use in osseous tissue. While the principles of the present disclosure are described below with respect to the insertion of the fixation device into a pedicle of a vertebra during orthopedic spine surgery, it should be understood that the fixation device of the present disclosure is suitable for insertion into any osseous tissue, such as the iliac of the pelvis, and use in a variety of surgical procedures. Accordingly, a person of ordinary skill in the art will readily appreciate that the size and/or shape of the fixation device, or components thereof, can be modified for proper alignment and fit within a desired osseous tissue.

Embodiments of the present disclosure will now be described in detail with reference to the drawings in which like reference numerals designate identical or corresponding elements in each of the several views. Throughout this description, the term "proximal" refers to a portion of a system, a device, or component thereof, that is closer to a user, and the term "distal" refers to the portion of the system, the device, or component thereof, that is farther from the user.

Referring now to FIGS. 1A-3, a fixation device 100 in accordance with an embodiment of the present disclosure is shown. The fixation device 100 is suitable for use during the treatment of bones (e.g., to fix the position of a bone, or portions thereof, or to maintain alignment of bone(s)), and may provide a point of fixation and/or facilitate the attachment of other devices (e.g., rods, plates, etc.) to the bone(s).

Figure 1B:
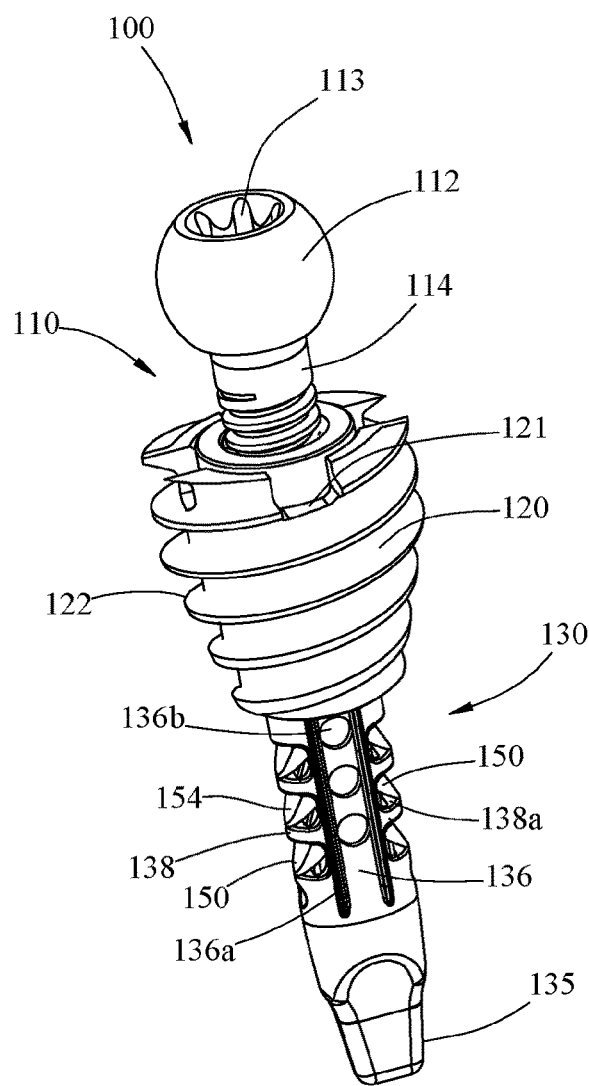
FIG. 1B is a perspective view of the fixation device of FIG. 1A.
Figure 1C:
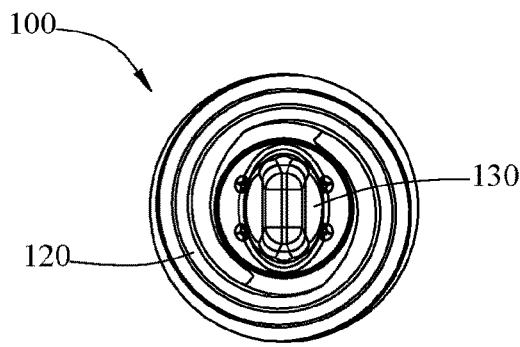
FIG. 1C is a bottom view of the fixation device of FIG. 1A.

The fixation device 100 extends along a longitudinal axis "X" and includes a post 110, a tapered cannula 120, and a shaft 130. The shaft 130 is engaged with the tapered cannula 120, and the post 110 is engaged with and movable relative to the shaft 130. The post 110 and shaft 130 are each partially disposed within the tapered cannula 120, with the post 110 extending proximally from the tapered cannula 120 and the shaft 130 extending distally from the tapered cannula 120. The fixation device 100 is movable between a closed or undeployed position, as shown in FIGS. 1A-1C, in which blades 150 (FIG. 3) of the fixation device 100 are disposed within the shaft 130 of the fixation device 100, and an open or deployed position, as shown in FIGS. 2A-2D, in which the blades 150 extend or protrude laterally through the shaft 130 of the fixation device 100.

Figure 3:
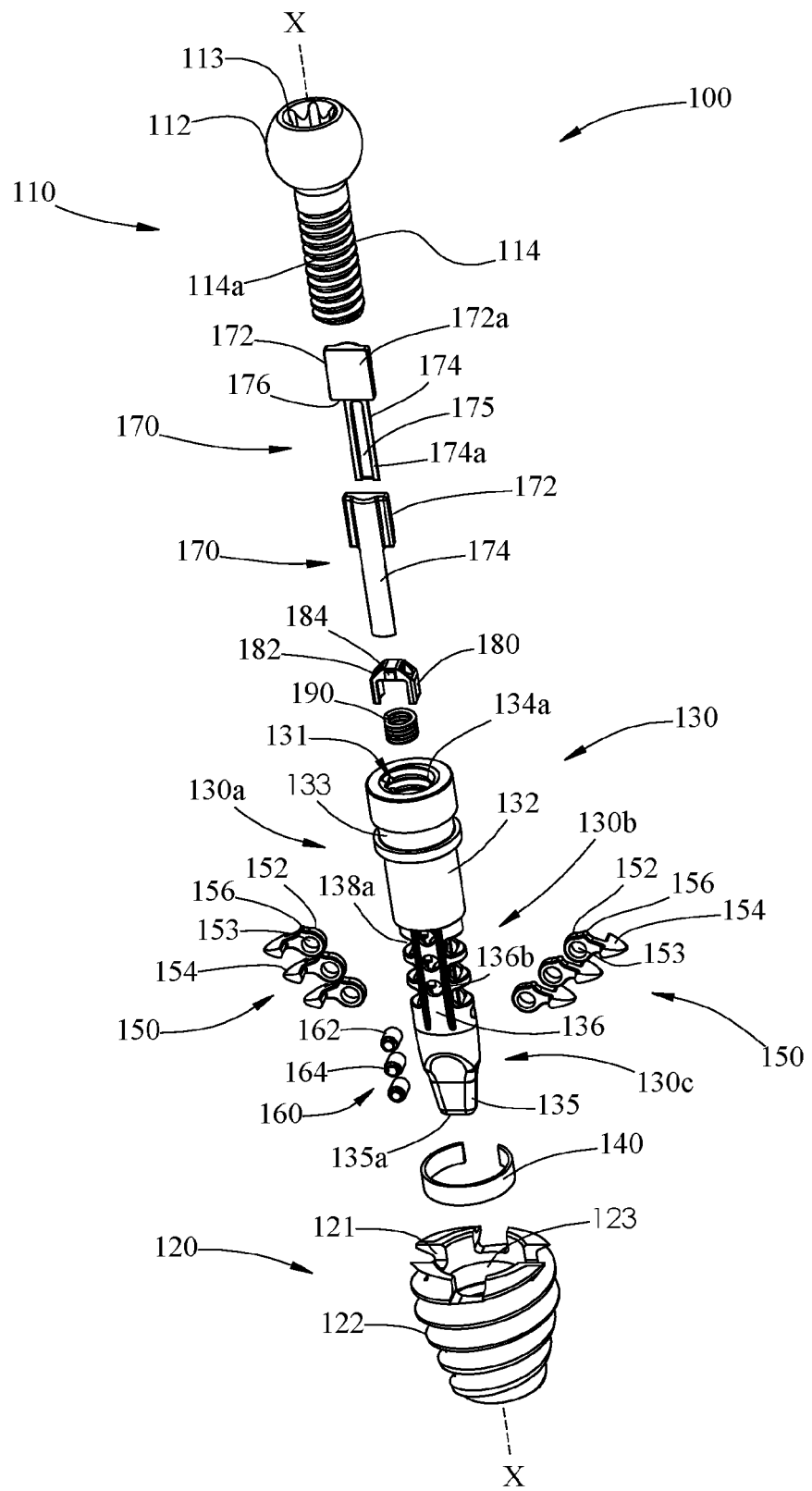
FIG. 3 is an exploded view of the fixation device of FIG. 1A.
Figure 4B:
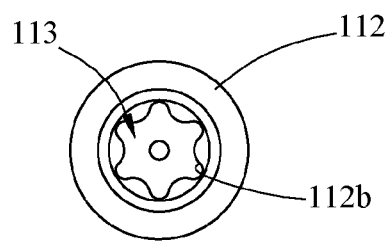
FIG. 4B is a top view of the post of FIG. 4A.
Figure 4A:
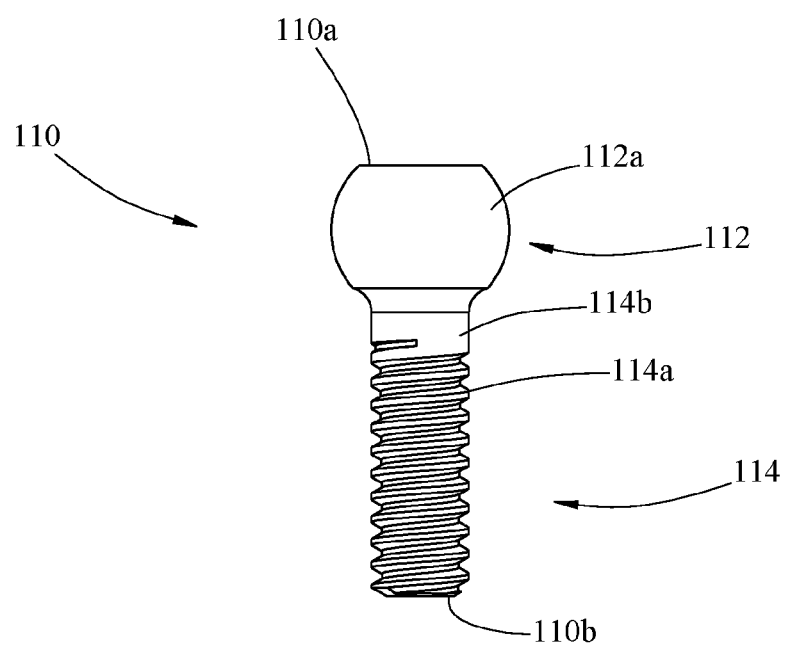
FIG. 4A is a side view of a post of the fixation device of FIG. 1A.

Turning now to FIGS. 3-4B, the post 110 includes a head 112 and an elongate body 114 extending distally from the head 112. The head 112 is substantially spherical or ball shaped. The head 112 includes an outer surface 112a that can be roughened (e.g., textured, grooved, etc.) to enhance the grip of a user or the attachment of another surgical device thereto, such as a modular screw assembly (see e.g., FIG. 12) which, in turn, may be coupled to other surgical devices (e.g., rods, plates, etc.). Suitable modular screw assemblies include, for example, taper lock or set screw housing systems such as those shown in U.S. Pat. Nos. 8,814,919 and 9,393,049, and/or modular head assemblies such as those shown in Int'l Appl. No. PCT/US18/14179, the entire content of each of which is incorporated by reference herein.

The head 112 can be of any shape and/or size suitable for manipulating the fixation device 100 into or out of an osseous tissue and/or facilitating attachment of other surgical devices thereto. For example, the head may have a substantially cylindrical shape including a threaded outer surface (e.g., the head may be an extension of the elongate body) configured for attachment of modular hardware, such as a complementary inner threaded attachment device (e.g., a modular attachment assembly) thereto.

The head 112 includes an opening 113 therein that is defined by an inner surface 112b of the head 112. The opening 113 extends through a proximal end 110a of the post 110 and is configured and dimensioned to receive an engagement tip 66 (FIG. 13) of a driving instrument 60 therein. The inner surface 112b of the head 112 may be multi-faceted (e.g., hexagonal or hexolobular in shape), keyed, or any other suitable configuration that is engageable with a suitable driving instrument to enable the driving instrument to control rotation of the post 110 and/or aid in the insertion or removal of the fixation device 100 into or out of osseous tissue. The opening 113 of the head 112 may have any geometric configuration that complements the engagement tip 66 of the driving instrument 60 thereby providing positive engagement between the head 112 and the driving instrument 60.

The elongate body 114 of the post 110 is substantially cylindrical in shape and includes a threaded outer surface 114a. In embodiments, the threaded outer surface 114a extends the entire length of the elongate body 114 and, in some embodiments, the elongate body 114 includes an unthreaded outer surface section 114b disposed adjacent to the head 112 of the post 110 to allow for securing of the fixation device 100 into bone and subsequent attaching of a modular head assembly 10 (FIG. 12) to the head 112 due to the unthreaded outer surface section 114b maintaining a gap between the distal end of the head 112 and a surface of the bone. The threaded outer surface 114a of the elongate body 114 is configured and dimensioned to engage a threaded inner surface 134a of the shaft 130.

Figure 5C:
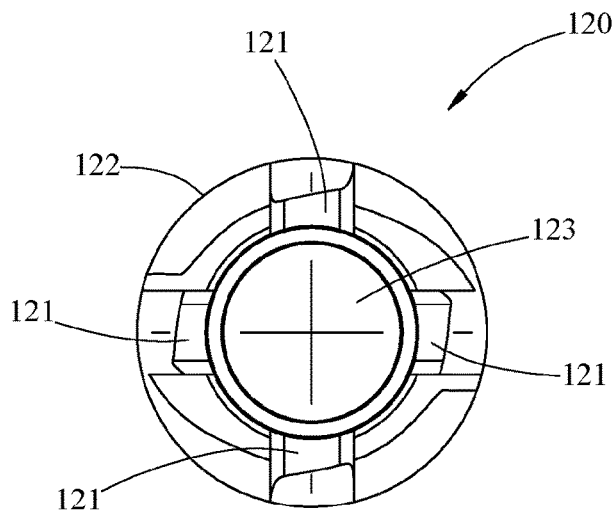
FIG. 5C is a top view of the tapered cannula of FIG. 5A.
Figure 5A:
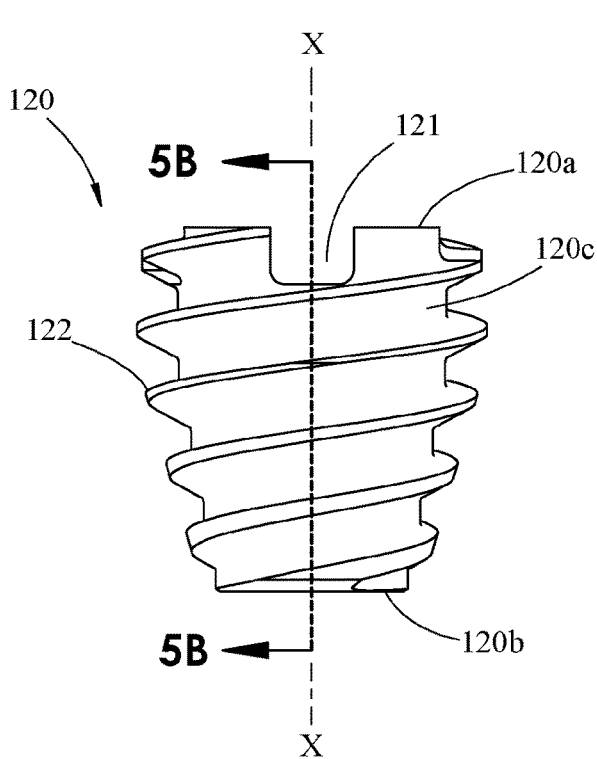
FIG. 5A is a side view of a tapered cannula of the fixation device of FIG. 1A.
Figure 5B:
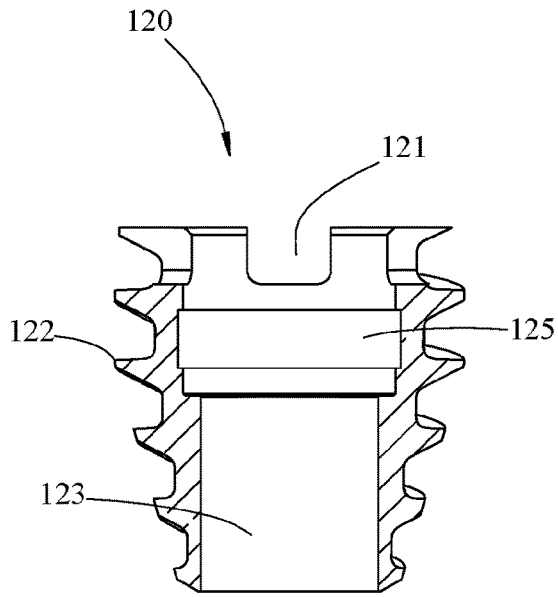
FIG. 5B is a cross-sectional view of the tapered cannula of FIG. 5A, taken along section line 5B-5B of FIG. 5A.

As shown in FIGS. 5A-5C, the tapered cannula 120 tapers distally from a proximal end 120a to a distal end 120b of the tapered cannula 120. It should be understood that the tapered cannula 120 may have any shape, size, and/or length suitable for insertion into a targeted osseous tissue. For example, the tapered cannula 120 may be configured and dimensioned such that when the fixation device 100 is inserted into osseous tissue, such as a pedicle of a vertebra, the tapered cannula 120 fits within or stays above the isthmus "I" of the pedicle "P" as shown, for example, in FIG. 11B, and can inhibit the fixation device 100 from breaching the osseous tissue.

The proximal end 120a of the tapered cannula 120 includes at least one cut-out 121 defined therein that is configured and dimensioned for engagement with an insertion instrument 70 (FIG. 14) to assist in the insertion or removal of the tapered cannula 120 into osseous tissue. As seen in FIGS. 5A-5C, the tapered cannula 120 includes four cut-outs 121 each having a substantially rectangular shape formed in the proximal end 120a of the tapered cannula 120. The cut-outs 121 are evenly spaced around the proximal end 120a of the tapered cannula 120 and disposed about 90 degrees out of phase with respect to one another. It should be understood that the tapered cannula 120 may include any number of cut-outs 121 (e.g., one, two, three, four, etc.) having any size and/or shape engageable with a suitable insertion instrument to enable the insertion instrument to control rotation of the tapered cannula 120 and/or aid in the insertion or removal of the fixation device 100 into or out of osseous tissue.

The tapered cannula 120 includes helical threads 122 extending from an outer surface 120c thereof that are configured to cut and/or thread into osseous tissue. The helical threads 122 may extend along the entire length of the tapered cannula 120, a portion of the length of the tapered cannula 120, or include regions of helical threads 122 disposed in spaced relation relative to each other along the length of the tapered cannula 120. The helical threads 122 can rotate clockwise (i.e., a right-handed thread) or counterclockwise (i.e., a left-handed thread) about the tapered cannula 120. It should be understood that the configuration, number, and/or orientation of the helical threads 122 may vary depending upon, for example, the desired cutting and/or retaining characteristics desired of the fixation device 100.

In embodiments, the helical threads 122 have a major diameter ranging from about 9 mm to about 13 mm, and in some embodiments, the major diameter of the helical threads 122 ranges from about 10 mm to about 12 mm. In embodiments, the major diameter of the helical threads 122 tapers distally along the length of the tapered cannula 120 at a ratio of the major diameter at the proximal end to the major diameter at the distal end in a range of about 1 to about 2, and in some embodiments, at a ratio in the range of about 1.4 to about 1.7. The angle of the taper, or taper angle, may vary and in embodiments, the taper angle is from about 10 degrees to about 60 degrees and, in some embodiments, the taper angle is from about 18 degrees to about 56 degrees.

Figure 2D:
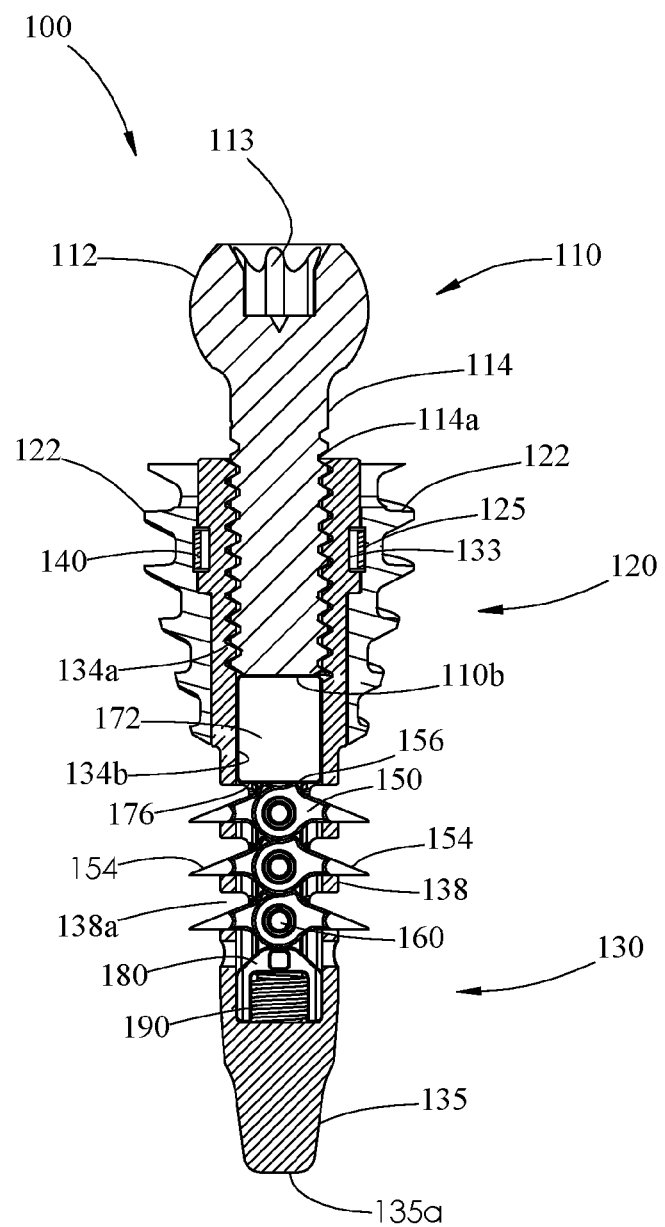
FIG. 2D is a cross-sectional view of the fixation device of FIG. 2A.

The tapered cannula 120 includes a bore 123 extending therethrough along the longitudinal axis "X" of the fixation device 100. As seen in FIGS. 2D, 3, and 5B, the bore 123 is configured and dimensioned to receive a proximal portion 130a of the shaft 130 therein. The bore 123 includes an annular groove 125 defined therein that is dimensioned to receive a snap ring 140 therein for retaining the proximal portion 130a of the shaft 130 within the tapered cannula 120.

Figure 6:
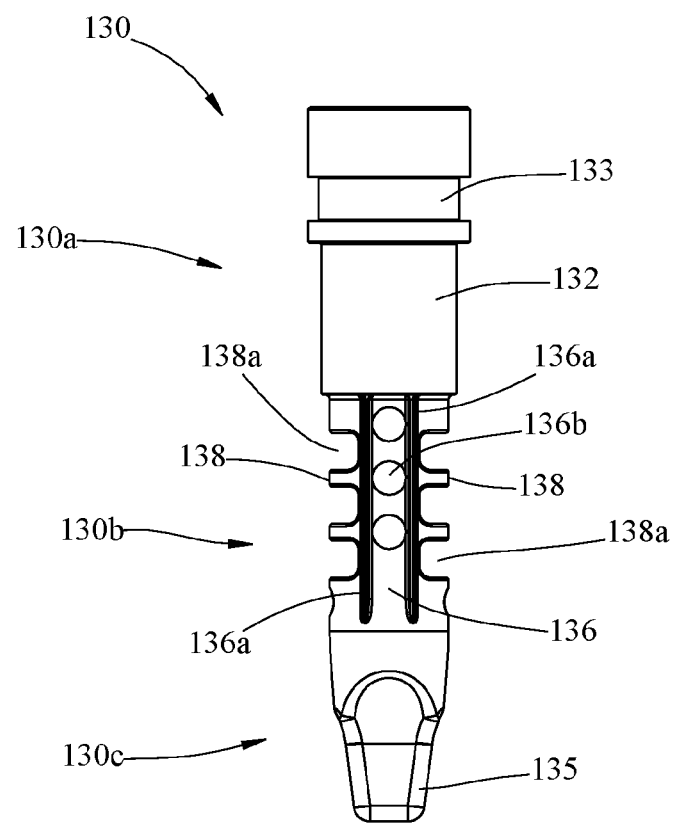
FIG. 6 is a side view of a shaft of the fixation device of FIG. 1A.

With reference now to FIGS. 2D, 3, and 6, the shaft 130 includes a proximal portion 130a, a central portion 130b, and a distal portion 130c. The proximal portion 130a of the shaft 130 includes an outer surface 132 configured and dimensioned to be received within the bore 123 of the tapered cannula 120. The outer surface 132 of the proximal portion 130a of the shaft 130 includes an annular groove 133 defined therein that is configured to receive the snap ring 140 therein. The snap ring 140 is configured and dimensioned to fit within the annular groove 133 of the shaft 130 and the annular groove 125 of the tapered cannula 120 to secure the shaft 130 to the tapered cannula 120 when the shaft 130 is received within the tapered cannula 120. The snap ring 140 can be disposed within the annular groove 133 of the shaft 130 and can expand into the annular groove 125 of the tapered cannula 120 when the annular grooves 133, 125 are aligned. The snap ring 140 can hold the tapered cannula 120 in place on the shaft 130 without limiting the ability of the tapered cannula 120 to rotate about the longitudinal axis "X" of the fixation device 100. This arrangement of the snap ring 140, the annular groove 133, and the annular groove 125 allows relative rotation between the shaft 130 and the tapered cannula 120.

The shaft 130 includes a channel 131 defined longitudinally through the proximal and central portions 130a, 130b of the shaft 130, and terminating within the distal portion 130c of the shaft 130. A first portion of the channel 131 is disposed within the proximal portion 130a of the shaft 130 and is defined by a threaded inner surface 134a configured to threadingly engage the threaded outer surface 114a of the elongate body 114 of the post 110, and an unthreaded region 134b, disposed distal to the threaded inner surface 134a, configured to receive heads 172 of aligners 170 therein.

The central portion 130b of the shaft 130 includes spines 136 (see e.g., FIG. 1A) disposed in opposed relation relative to each other and extending longitudinally between the proximal portion 130a and the distal portion 130c of the shaft 130. Each spine 136 can include an external rib 136a disposed on and extending longitudinally along the spine 136 to provide support (e.g., stiffening) to the spine 136. In embodiments, each spine 136 includes external ribs 136a disposed on lateral sides of the spine 136.

As shown in FIGS. 3 and 6, each spine 136 may include one or more access holes 136b defined therethrough and spaced along the length of the spine 136. The number of access holes 136b can correspond to the number of pins 160 utilized to secure the blades 150 to the shaft 130, as described in detail below. The access holes 136b can be any size and/or shape, such as circular or rectangular, so long as the dimension allows for the pins 160 to be passed therethrough or retained therein for assembly of the blades 150 therein.

With continued reference to FIGS. 3 and 6, the central portion 130b of the shaft 130 also includes ledges 138 disposed in opposed relation relative to each other and interconnecting the spines 136. Each ledge 138 extends laterally in an annular (e.g., semi-annular) configuration from one spine 136 to the other spine 136. Together, the spines 136 and the ledges 138 define a second portion of the channel 131 therein that is configured to receive the blades 150, the pins 160, and the aligners 170. A pair of ledges 138 is longitudinally separated from an adjacent pair of ledges 138 or the proximal or distal portions 130a, 130b of the shaft 130 by a longitudinal distance defining blade openings 138a therebetween. The shaft 130 can include any number of ledges 138 (e.g., one, two, three, four, five, etc.) so long as the shaft 130 includes a number of blade openings 138a corresponding with the number of blades 150 of the fixation device 100.

The blade openings 138a of the shaft 130 can be any size or shape so long as each blade opening 138a can contain a blade 150 therein. In embodiments, the blade openings 138a are rectangular in shape, however, the blade openings 138a can be any shape that is defined by the ledges 138 and the spines 136. In the closed position, as shown in FIGS. 1A-1C, each of the blades 150 can be contained within a respective blade opening 138a of the shaft 130 with a wing portion 154 of the blade 150 resting on the ledge 138 disposed distal of the blade 150 such that the blade 150 does not extend laterally past the ledge 138. The ledge 138 is configured and dimensioned so that when the fixation device 100 transitions from the closed position to the open position, the blade 150 can slide against or push off the ledge 138 and extend laterally beyond the ledge 138 in the open position, as shown in FIGS. 2A-2D.

Figure 7A:
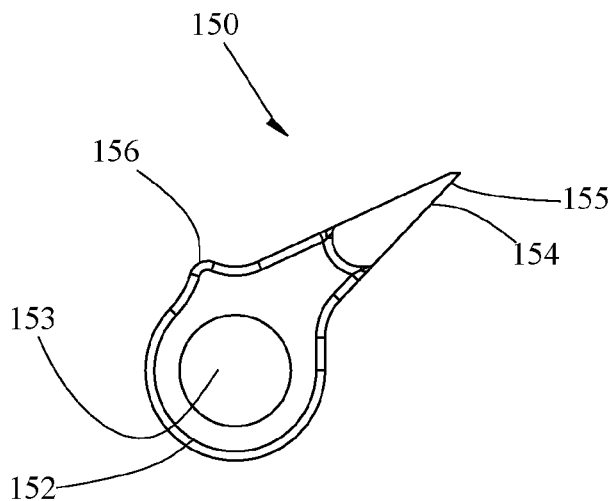
FIG. 7A is a side view of a blade of the fixation device of FIG. 1A.
Figure 7B:
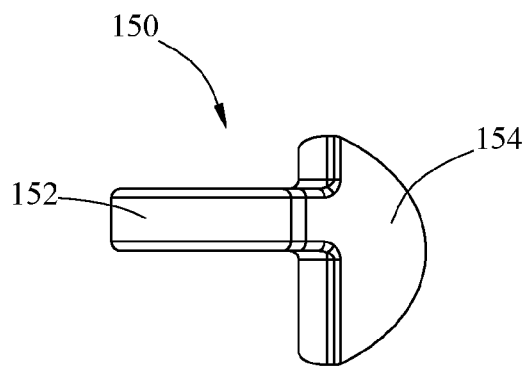
FIG. 7B is a bottom view of the blade of FIG. 7A.

As shown in FIGS. 7A and 7B, each blade 150 includes a substantially annular body portion 152 defining an opening 153 therethrough that is configured and dimensioned to receive a pin 160 (FIG. 8) therethrough, and a wing portion 154 extending from the body portion 152. The wing portion 154 tapers away from the body portion 152 and defines an edge 155 at an end thereof that is configured to cut and/or thread into osseous tissue. The wing portion 154 may extend along a plane that is perpendicular to a plane defined through the body portion 152. A notch or protrusion 156 extends from the body portion 152 and is configured to abut against a longitudinally adjacent blade 150 or a head 172 of an aligner 170 when assembled within the shaft 130 to inhibit rotation thereof when in the open position.

Figure 8:
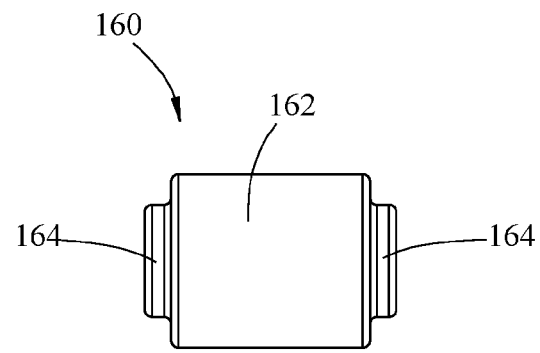
FIG. 8 is a side view of a pin of the fixation device of FIG. 1A.

As shown in FIG. 8, each pin 160 has a cylindrical shape and includes a central portion 162 having a first diameter and end portions 164 extending from opposed sides of the central portion 162. Each of the end portions 164 has a second diameter that is smaller than the first diameter of the central portion 162. The pin 160 can be any size or shape so long as the central portion 162 of the pin 160 fits into the opening 153 (FIG. 7A) of the blade 150 and the blade 150 is rotatable about the pin 160.

During assembly of the blades 150 within the shaft 130 of the fixation device 100, as shown in FIGS. 2D and 3, the pins 160 are inserted through the access holes 136a of one of the spines 136 such that the central portion 162 of each of the pins 160 extends through the openings 153 of the respective blades 150 that are paired and oppositely oriented in laterally opposed blade openings 138a of the shaft 130, and the end portions 164 of each of the pins 160 are positioned adjacent to and laterally inward of the respective access holes 136a of the spines 136. The aligners 170 are then positioned within the shaft 130 to retain the pins 160 therein and permit axial movement of the pins 160 within the shaft 130, as described in detail below.

Figure 9A:
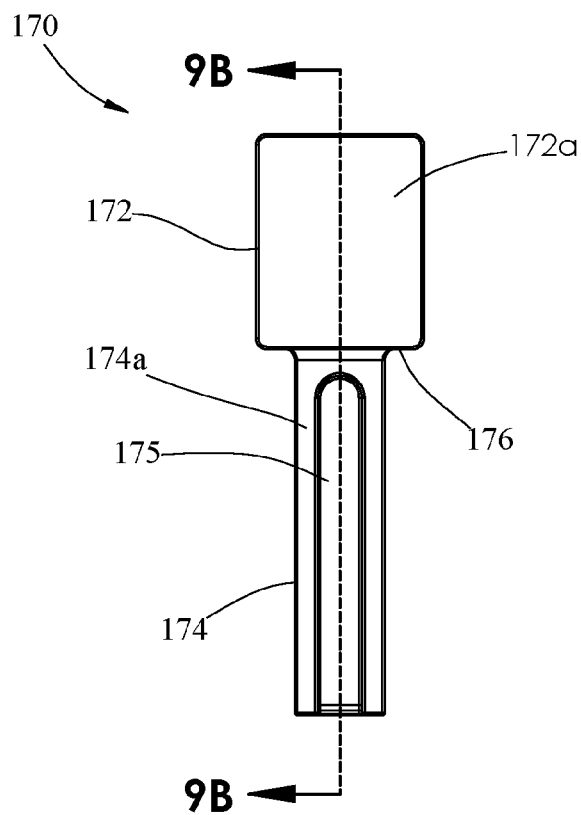
FIG. 9A is a front view of an aligner of the fixation device of FIG. 1A.
Figure 9B:
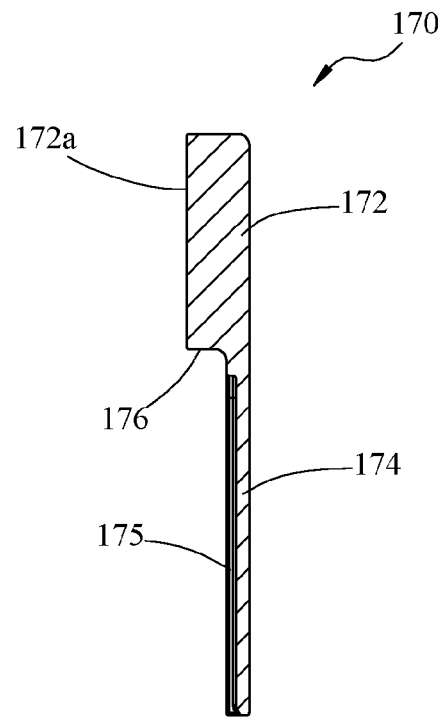
FIG. 9B is a cross-sectional view of the aligner of FIG. 9A, taken along section line 9B-9B of FIG. 9A.

As shown in FIGS. 9A and 9B, each aligner 170 includes a head 172 and an elongate tail 174 extending from the head 172. The head 172 includes a flat surface 172a and the elongate tail 174 includes a flat surface 174a having a groove 175 defined longitudinally therein. The head 172 further includes a distal surface 176 defining a step between the head 172 and the elongate tail 174.

As seen in FIGS. 2D and 3, the aligners 170 are positioned within the shaft 130 with the flat surfaces 172a of the heads 172 abutting each other, and the flat surfaces 174a of the elongate tails 174 facing each other. The heads 172 are disposed within the unthreaded region 134b of the proximal portion 130a of the shaft 130, and the elongated tails 174 extend into the central portion 130b of the shaft 130 parallel and adjacent to the spines 136. The end portions 164 of the pins 160 are disposed within the grooves 175 of the aligners 170 such that the elongate tails 174 block the access holes 136b of the spines 136 to prevent the pins 160 from being removed from within the shaft 130. The distal surfaces 176 of the heads 172 of the aligners 170 abut against the blades 150 disposed adjacent thereto (i.e., the blades 150 disposed in the proximal-most position within the shaft 130), such that axial movement of the aligners 170 in a distal direction causes the pins 160 and thus, the blades 150 to translate axially within the shaft 130. As discussed above, the wing portion 154 of each of the blades 150 abuts a respective ledge 138 which forces the blade 150 to extend laterally beyond the ledge 138 when the blade 150 transitions from the closed position to the open position. The blade 150 rotates about the respective pin 160 until the notch 156 of the blade 150 abuts an adjacent blade 150 positioned proximally of the notch 156 or the distal surface 176 of the head 172 of the aligner 170 to prevent over-rotation of the blade 150.

With continued reference to FIGS. 2D and 3, the distal portion 130c of the shaft 130 includes a tip 135. The tip 135 tapers distally and terminates at a blunted end 135a. Other configurations of the tip 135 are contemplated. For example, the tip 135 may have a conical shape terminating at a blunted or pointed end. A pointed or sharpened end may, for example, assist in probing osseous tissue.

Figure 10A:
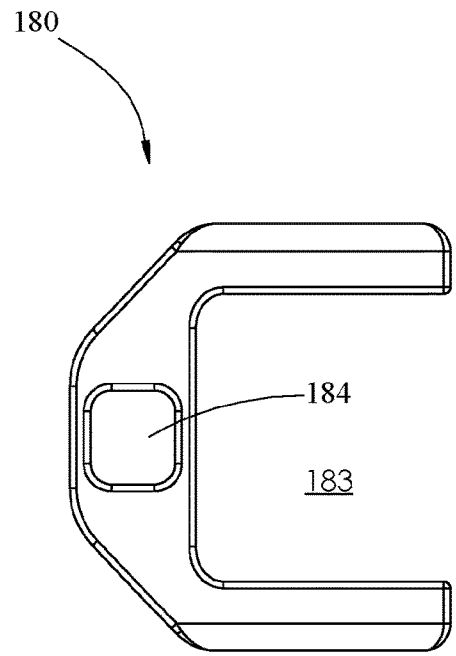
FIG. 10A is a side view of a cap of the fixation device of FIG. 1A.
Figure 10B:
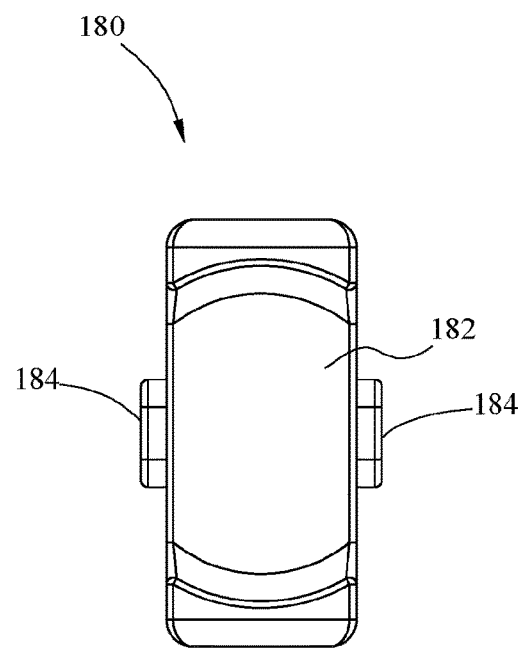
FIG. 10B is a top view of the cap of FIG. 10A.
Figure 10C:
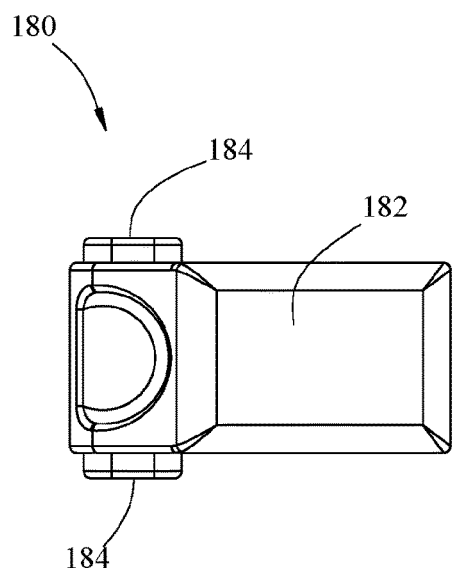
FIG. 10C is an end view of the cap of FIG. 10A.

A cap 180 and a spring 190 are disposed within a third portion of the channel 131 defined in the distal portion 130c of the shaft 130. As shown in FIGS. 10A-10C, in conjunction with FIGS. 2D and 3, the cap 180 includes a generally u-shaped body 182 including bosses 184 extending from opposed sides of the body 182. The bosses 184 are configured and dimensioned to fit within the grooves 175 of the aligners 170 so that the cap 180 can translate axially within the grooves 175. The body 182 further includes a slot 183 defined therein. The slot 183 is configured and dimensioned to receive the spring 190 therein. The spring 190 is configured to expand and apply a force on the cap 180 which, in turn, applies a force on the aligners 170. Axial movement of the aligners 170 in a proximal direction causes the pins 160 to translate axially within the shaft 130 which, in turn, cause the blades 150 to also rotate around the pins 160 thereby retracting the wing portion 154 of each of the blades 150 along the respective ledge 138 and towards the longitudinal axis "X" of the shaft 130 such that the blades 150 transition from the open position to the closed position.

In a method of using the fixation device 100 in accordance with an embodiment of the present disclosure, an insertion hole is formed in osseous tissue. A user drills or otherwise forms an insertion hole into osseous tissue using known devices and techniques (e.g., punching, cutting, coring, etc.). For example, an insertion hole may be formed by preparing the surface of the osseous tissue with a burr or other like instrument and then using an awl or other like instrument to start the insertion hole in such anatomy as a pedicle of a vertebra.

Figure 11A:
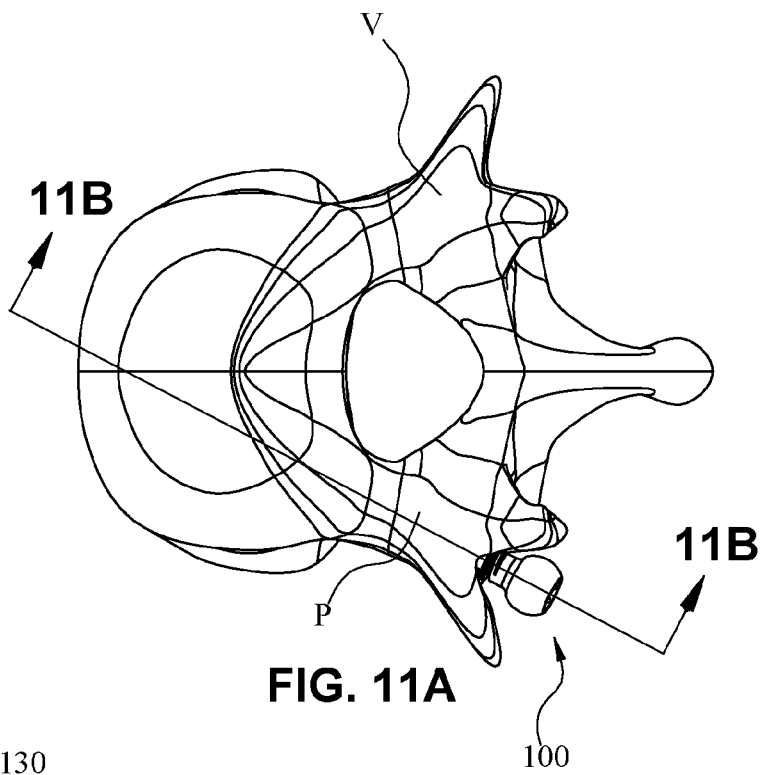
FIG. 11A is an isometric view illustrating the fixation device of FIG. 2A secured to osseous tissue in accordance with an embodiment of the present disclosure.
Figure 11B:
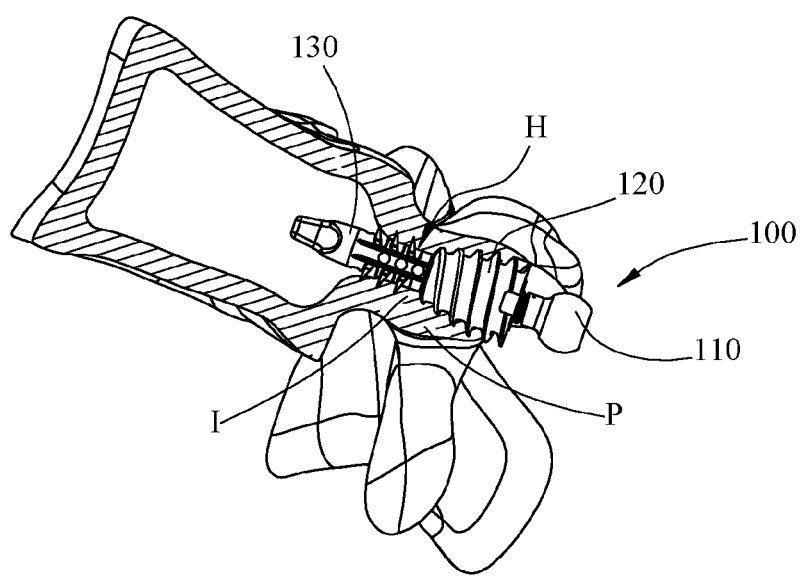
FIG. 11B is a cross-sectional view of the fixation device and osseous tissue of FIG. 11A, taken along section line 11B-11B of FIG. 11A.

As shown in FIGS. 11A and 11B, an insertion hole "H" is formed in a vertebral body "V," namely, in the isthmus "I" of a pedicle "P." The fixation device 100, disposed in the closed position of FIGS. 1A-1C, is then inserted into the insertion hole "H". The user can insert the fixation device 100 into the insertion hole "H" until the tapered cannula 120 fits within or stays above the isthmus "I" of the pedicle "P", and the shaft 130 extends below the isthmus "I".

The fixation device 100 may be manipulated by imparting rotational force(s) thereto. A rotational force can be applied to the post 110 by inserting the engagement tip 66 (FIG. 13) of the driving instrument 60 into the opening 113 defined in the head 112 of the post 110 to engage the inner surface 112*b* defining the opening 113 and to apply a rotational force thereto. As discussed above, the threaded outer surface 114*a* of the post 110 is engaged with the threaded inner surface 134*a* of the shaft 130 such that rotation of the post 110 about the longitudinal axis "X" moves the post 110 axially with respect to the shaft 130. In this manner, the post 110 is moved distally within the shaft 130 until a distal end 110*b* of the post 110 abuts against the heads 172 of the aligners 170 as seen, for example, in FIG. 2D. The aligners 170 are moved distally by the post 110 to rotate the blades 150 disposed within the shaft 130 about the respective pins 160, forcing the blades 150 to push against the respective ledges 138 and to extend laterally beyond the ledges 138 into the open position.

The rotational force is inhibited when the notches 156 of the blades 150 abut against an adjacent blade 150 or the distal surface 176 of the aligners 170, as discussed above. Additionally, as the rotational force is applied, the pins 160 and the blades 150 translate axially within the grooves 175 of the aligners 170 and push against the cap 180 which, in turn, compresses the spring 190. As can be seen in FIG. 2C, when the blades 150 are extended in the open position, the fixation device 100 has an elliptical shape mimicking the shape of the pedicle "P". The blades 150, in the open position, can cut into adjacent bone further securing the fixation device 100 to the osseous tissue.

A rotational force can be applied to the tapered cannula 120 by placing the plurality of tabs 76 (FIG. 14) of the insertion instrument 70 into the cut-outs 121 of the tapered cannula 120, as described above, and applying a rotational force to the insertion instrument 70 that rotates the tapered cannula 120 about the longitudinal axis "X" so that the helical threads 122 of the tapered cannula 120 engage with the osseous tissue (e.g., the pedicle "P").

Further, a user can apply an opposite rotational force to the post 110 (e.g., via the driving instrument 60) and/or to the tapered cannula 120 (e.g., via the insertion instrument 70) to adjust the placement of the fixation device 100 within the osseous tissue or to remove the fixation device 100 completely therefrom. Opposite rotation of the post 110 causes the post 110 to move proximally within the shaft 130 allowing the spring 190 to expand and force the cap 180 and thus, the aligners 170, the pins 160, and the blades 150 to translate axially within the shaft 130. As the blades 150 rotate about the pins 160, but in an opposite direction, the blades 150 retract into the blade openings 138*a* of the shaft 130 and back into the closed position as shown, for example, in FIG. 1C.

The fixation device 100 is fully inserted into osseous tissue with minimal and/or reduced time and/or effort compared to traditional bone screws. The tapered cannula 120 of the fixation device 100 provides improved toggling strength over a conventional bone screw as the tapered cannula 120 is engaged with more bone above the pedicle. The tapered cannula 120 has a greater surface area than a conventional bone screw and thus, may provide improved engagement between the tapered cannula 120 and the osseous tissue which, in turn, may improve securement of the tapered cannula 120 in bone and reduce the possibility of the fixation device 100 being pulled out of the osseous tissue. The tapered cannula 120 of the fixation device 100 may also provide improved securement, as compared to using a traditional bone screw, in osseous tissue having a relatively low density, and/or increased resistance to pull out in view of possible load values that may be placed on the osseous tissue when, for example, additional mechanical hardware (e.g., screws, rods, etc.) are coupled thereto.

The fixation device 100 may also be used in situations where a hole or an opening exists in a bone with a diameter too large for a traditional bone screw. This may result from a previous bone anchor installation and removal where the opening has a diameter unsuitable for securing a bone screw therein or the opening has an incorrect orientation for proper securement of a bone screw.

Figure 12:
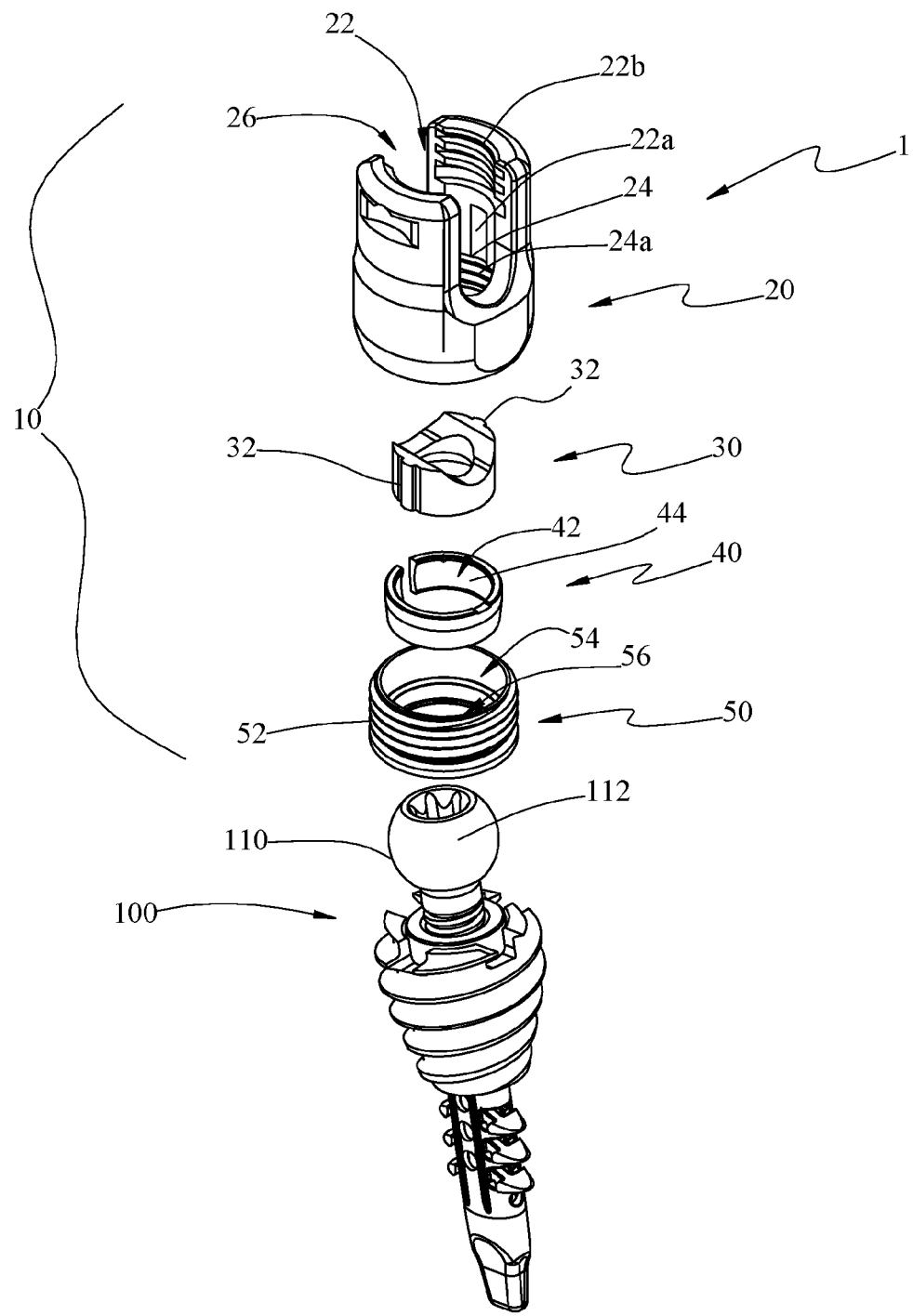
FIG. 12 is a perspective view of the fixation device of FIG. 2A and a modular head assembly, with parts separated, in accordance with an embodiment of the present disclosure.

In embodiments, a surgical device, such as a modular head assembly 10 as shown in FIG. 12, may be coupled to the fixation device 100 such that other surgical devices (e.g., rods, plates, etc.) may be coupled thereto. FIG. 12 illustrates a surgical fixation system 1 including the modular head assembly 10 and the fixation device 100. The modular head assembly 10 includes a housing 20, an anvil 30, a snap ring 40, and an insert 50. The modular head assembly 10 is assembled by aligning a pair of tabs 32 of the anvil 30 with a corresponding pair of slots 22*a* of a through-hole 22 of the housing 20, and advancing the anvil 30 in a proximal direction within the through-hole 22 such that the pair of tabs 32 engages the pair of slots 22*a*. Next, the snap ring 40 is placed adjacent a counterbore 24 of the housing 20 and advanced in a proximal direction such that the snap ring 40 is slidably received therein. With the snap ring 40 received within the counterbore 24, the insert 50 is initially placed adjacent the counterbore 24 of the housing 20, and then rotated in a first direction such that a plurality of threads 52 of the insert 50 threadably engages a corresponding plurality of threads 24*a* of the counterbore 24 of the housing 20. The insert 50 is further rotated until the insert 50 is fully received within the counterbore 24. In this position, the anvil 30 is in a proximal most position and the snap ring 40 is disposed within a first counterbore 54 of the insert 50 such that the snap ring 40 is in a first, uncompressed state.

With the fixation device 100 inserted into bone, as discussed above, the assembled modular head assembly 10 is placed adjacent the head 112 of the post 110 of the fixation device 100. The modular head assembly 10 is then advanced in a distal direction such that the head 112 of the fixation device 100 is received within a bore 56 of the insert 50, and thereafter, within a lumen 42 of the snap ring 40. As the head 112 of the fixation device 100 advances within the lumen 42 of the snap ring 40, the head 112 causes the snap ring 40 to expand (e.g., the diameter enlarges) to accept the head 112 therein. A concave inner surface 44 of the lumen 42 conforms to the spherical profile of the head 112 such that the diameter of the snap ring 40 reduces from an expanded state during insertion of the head 112 therein to a compressed state where the inner diameter of the lumen 42 conforms to the diameter of the head 112 and provides a compressive force thereon. Thereafter, the axial orientation of the fixation device 100 relative to the modular head assembly 10 may be adjusted and locked, for example, when a suitable spinal rod (not shown) is secured within a U-shaped slot 26 of the housing 20 using a suitable set screw (not shown) threadingly engaged with a plurality of threads 22b of the throughhole 22 of the housing 20.

Figure 13:
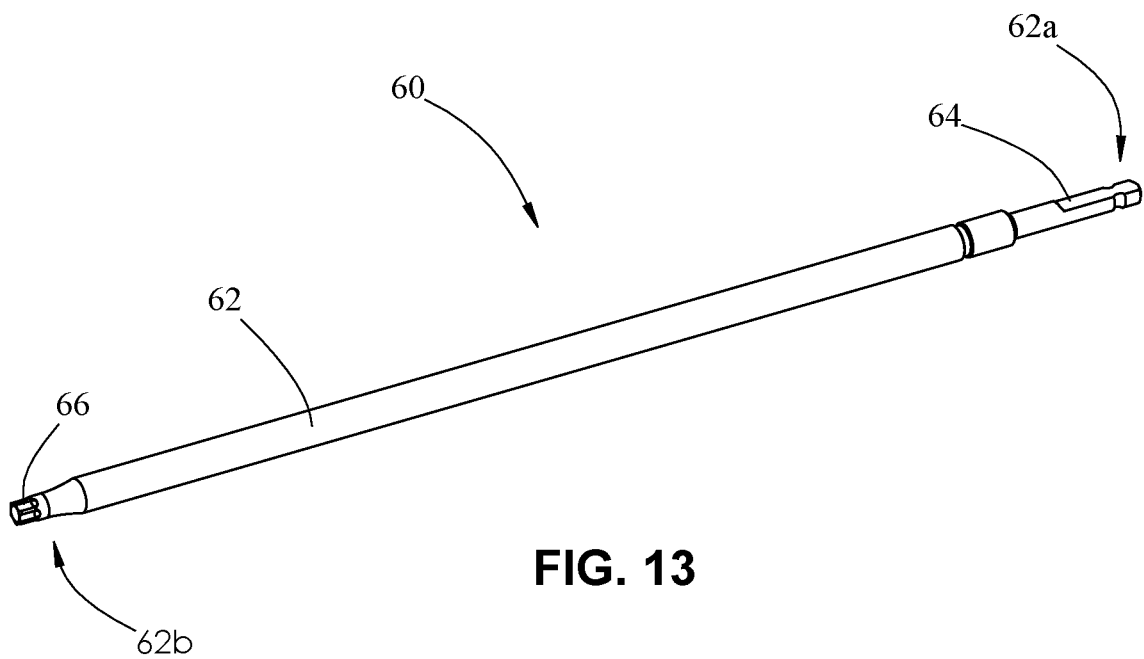
FIG. 13 is a perspective view of a driving instrument for rotating a post of the fixation device of FIG. 1A.

With reference to FIG. 13, a driving instrument or driver suitable for use with the post 110 of the fixation device 100 is provided and generally identified by reference numeral 60. The driving instrument 60 includes an elongate shaft 62 having a proximal portion 62a and an opposed distal portion 62b. The proximal portion 62a of the elongate shaft 62 defines a handle attachment feature 64 that is configured to enable selective rotation of the driving instrument 60 (e.g., by gripping the handle attachment feature 64 and applying rotational force thereto) by a user. A driver handle (not shown) may be applied to the handle attachment feature 64 to enable the selective application of the rotational force to the driving instrument 60 (e.g., a user grips the driver handle and applies a rotational force thereto). The distal portion 62b of the driver 60 tapers to a driving, but reduced diameter engagement region or tip 66. The engagement tip 66 includes protrusions and recesses that are complementary to the opening 113 of the head 112 of the post 110 of the fixation device 100. Once the engagement tip 66 is inserted into the opening 113, rotation of the driving instrument 60 results in rotation of the post 110. Thus, the driving instrument 60 is capable of rotating the post 110 for deployment or retraction of the blades 150 of the fixation device 100. It is envisioned that driving instrument 60 may also be used with a set screw (not shown) for inserting and/or removing a set screw from the housing 20 of the modular head assembly 10.

Figure 14:
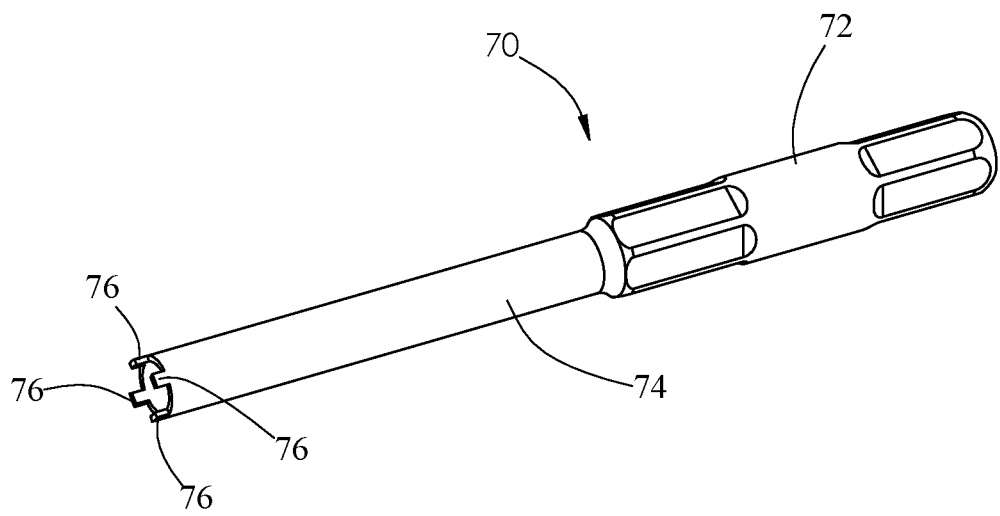
FIG. 14 is a perspective view of an insertion instrument for rotating a tapered cannula of the fixation device of FIG. 1A.

With reference to FIG. 14, an insertion instrument or inserter suitable for use with the tapered cannula 120 of the fixation device 100 is provided and generally identified by reference numeral 70. The insertion instrument 70 includes a handle 72 and an elongated shaft 74 extending distally from the handle 72. The elongated shaft 74, which may have a tubular configuration, including a plurality of spaced-apart tabs 76 (radially and/or circumferentially spaced apart) that extend distally from the elongated shaft 74 to a distal end of the insertion instrument 70. The plurality of spaced-apart tabs 76 are configured to be received within the cut outs 121 of the tapered cannula 120, and may be complementary thereto, so that manual rotation of the insertion instrument 70 rotates the tapered cannula 120 about the longitudinal axis "X" of the fixation device 100 for driving the tapered cannula 120 into or out of osseous tissue when the insertion instrument 70 is coupled to the tapered cannula 120.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown and described in connection with certain embodiments may be combined with the elements and features of certain other embodiments without departing from the scope of the present disclosure, and that such modifications and variation are also included within the scope of the present disclosure. Accordingly, the subject matter of the present disclosure is not limited by what has been particularly shown and described. Thus, other embodiments are within the scope of the following claims.

What is claimed is:

1. A fixation device comprising:
a tapered cannula defining a bore therethrough;
a shaft including a proximal portion disposed within the bore of the tapered cannula, and central and distal portions extending distally from the tapered cannula, the distal portion being entirely unthreaded, the proximal portion including a threaded inner surface defined therein, the shaft including blades disposed within the central portion and distal of the tapered cannula, the blades movable between a closed position in which the blades are disposed within the shaft and an open position in which the blades extend laterally through the shaft; and
a post including a threaded outer surface threadingly engaged with the threaded inner surface of the shaft, the post movable longitudinally within the shaft to transition the blades between the closed and open positions.

2. The fixation device according to claim 1, further comprising a snap ring disposed within an annular groove defined in the bore of the tapered cannula and an annular groove defined in an outer surface of the shaft.

3. The fixation device according to claim 1, wherein the central portion of the shaft defines blade openings therein and, when the blades are disposed in the open position, each of the blades extends through one of the blade openings.

4. The fixation device according to claim 3, wherein the central portion of the shaft includes spines disposed in opposed relation relative to each other and extending longitudinally between the proximal and distal portions of the shaft.

5. The fixation device according to claim 4, wherein the central portion of the shaft includes ledges that laterally interconnect the spines.

6. The fixation device according to claim 5, wherein, when the blades are disposed in the closed position, a portion of each of the blades rests against the respective ledge disposed distal of the blade.

7. The fixation device according to claim 3, wherein each blade includes a body portion defining an opening therethrough and a wing portion extending from the body portion.

8. The fixation device according to claim 7, wherein each blade includes a notch extending from the body portion, the notch configured to inhibit rotation of the blade when the blade reaches the open position.

9. The fixation device according to claim 7, further comprising pins extending through the openings defined in the body portions of the blades, the blades rotatable around the pins.

10. The fixation device according to claim 9, further comprising aligners wherein each aligner includes a head disposed within the proximal portion of the shaft, an elongate tail extending into the central portion of the shaft, and a groove extending longitudinally therein, wherein end portions of each of the pins are disposed within the grooves of the aligners.

11. The fixation device according to claim 10, wherein the heads of the aligners are disposed adjacent to and distal of the post, and longitudinal movement of the post causes longitudinal movement of the aligners, the pins, and the blades.

12. The fixation device according to claim 11, wherein each blade rotates about the respective pin when the wing portion of the blade contacts a portion of the shaft defining the blade opening in which the respective blade is disposed.

13. The fixation device according to claim 10, further comprising a cap disposed within the distal portion of the shaft, the cap including bosses extending from opposed sides of a body, the bosses disposed within the grooves of the aligners.

14. The fixation device according to claim 13, further comprising a spring disposed within a slot of the cap, the spring being compressed by the cap when the blades are in the open position and the spring applying a proximal force on the cap when the blades are in the closed position.

15. A method of securing a fixation device to osseous tissue, comprising:
 inserting a distal portion of a shaft and a tapered cannula of a fixation device into an insertion hole in osseous tissue, the shaft including a proximal portion disposed within a bore of the tapered cannula, the fixation device disposed in a closed position in which blades are disposed within a central portion of the shaft distal of the tapered cannula, the distal portion being entirely unthreaded; and
 applying a force to a post of the fixation device to move the post distally, the post engaged with and longitudinally movable relative to the shaft such that distal movement of the post relative to the shaft causes the fixation device to transition from the closed position to an open position in which the blades extend laterally through the shaft and engage the osseous tissue.

16. The method according to claim 15, wherein applying the force to the post includes rotating the post relative to the shaft, the post and the shaft threadingly engaged with each other.

17. The method according to claim 15, wherein applying the force to the post includes inserting an engagement tip of a driving instrument into an opening defined in a head of the post.

18. The method according to claim 15, further comprising applying a force to the post to move the post proximally relative to the shaft to cause the fixation device to transition from the open position back to the closed position.

19. The method according to claim 15, further comprising applying a rotational force to the tapered cannula to engage helical threads disposed on an outer surface of the tapered cannula with the osseous tissue.

20. The method according to claim 19, wherein applying the rotational force to the tapered cannula includes inserting tabs of an insertion instrument into cut-outs defined in a proximal end of the tapered cannula.

\* \* \* \* \*